United States Patent
Helland et al.

(10) Patent No.: US 6,760,619 B1
(45) Date of Patent: Jul. 6, 2004

(54) TWO LEAD UNIVERSAL DEFIBRILLATION, PACING AND SENSING SYSTEM

(75) Inventors: John R. Helland, Saugus, CA (US); Gene A. Bornzin, Simi Valley, CA (US); Eric Falkenberg, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 279 days.

(21) Appl. No.: 09/945,449

(22) Filed: Aug. 31, 2001

(51) Int. Cl.$^7$ .............................................. A61N 1/368
(52) U.S. Cl. ............................................. 607/4; 607/123
(58) Field of Search ........................... 607/4, 5, 122, 607/123, 28, 9, 15, 18, 119

(56) References Cited

U.S. PATENT DOCUMENTS

| | | | |
|---|---|---|---|
| 4,548,203 A | 10/1985 | Tacker, Jr. et al. | 128/419 D |
| 4,932,407 A | 6/1990 | Williams | 128/419 D |
| 5,111,811 A | 5/1992 | Smits | 128/419 D |
| 5,174,289 A | 12/1992 | Cohen | 128/419 PG |
| 5,235,978 A | 8/1993 | Hirschberg et al. | 607/5 |
| 5,267,560 A | 12/1993 | Cohen | 607/25 |
| 5,314,430 A | 5/1994 | Bardy | 607/5 |
| 5,350,404 A * | 9/1994 | Adams et al. | 607/5 |
| 5,366,494 A | 11/1994 | Holleman et al. | 607/119 |
| 5,411,524 A * | 5/1995 | Rahul | 607/4 |
| 5,411,529 A * | 5/1995 | Hudrlik | 607/6 |
| 5,423,865 A | 6/1995 | Bowald et al. | 607/5 |
| 5,431,683 A | 7/1995 | Bowald et al. | 607/5 |
| 5,466,254 A | 11/1995 | Helland | 607/123 |
| 5,531,764 A | 7/1996 | Adams et al. | 607/5 |
| 5,545,204 A | 8/1996 | Cammilli et al. | 607/123 |
| 5,662,697 A * | 9/1997 | Li et al. | 607/122 |
| 5,720,768 A | 2/1998 | Verboven-Nelissen | 607/9 |
| 5,800,465 A | 9/1998 | Thompson et al. | 607/9 |
| 5,814,079 A | 9/1998 | Kieval | 607/4 |
| 5,814,081 A | 9/1998 | Ayers et al. | 607/5 |
| 5,836,975 A | 11/1998 | DeGroot | 607/5 |
| 5,836,976 A | 11/1998 | Min et al. | 607/6 |
| 5,865,838 A | 2/1999 | Obel et al. | 607/5 |
| 5,902,324 A | 5/1999 | Thompson et al. | 607/9 |
| 5,902,329 A | 5/1999 | Hoffmann et al. | 607/121 |
| 5,913,887 A | 6/1999 | Michel | 607/123 |
| 5,935,159 A | 8/1999 | Cross, Jr. et al. | 607/116 |
| 5,964,795 A | 10/1999 | McVenes et al. | 607/122 |
| 5,968,079 A | 10/1999 | Warman et al. | 607/5 |
| 5,978,704 A | 11/1999 | Ideker et al. | 607/5 |
| 5,987,354 A | 11/1999 | Cooper et al. | 607/5 |
| 5,999,853 A | 12/1999 | Stoop et al. | 607/9 |

(List continued on next page.)

FOREIGN PATENT DOCUMENTS

| | | | |
|---|---|---|---|
| EP | 0813889 A2 | 12/1997 | A61N/1/368 |
| WO | WO 00/33914 | 6/2000 | A61N/1/368 |

*Primary Examiner*—Angela D. Sykes
*Assistant Examiner*—Joseph S Machuga

(57) ABSTRACT

An implantable cardiac stimulation system senses electrical activity of all four chambers of the heart and delivers pacing and defibrillation pulses to all four chambers of the heart. The system includes a lead system consisting of first and second leads. The first lead includes a right ventricular pacing electrode, a right ventricular defibrillation electrode, and a right atrial defibrillation lead. The second lead is implantable in the coronary sinus of the heart and includes a left ventricular pacing electrode, a left ventricular defibrillation electrode, a left atrial pacing electrode, and a left atrial defibrillation electrode. A right atrial pacing electrode is carried by one of the first and second leads. The system further includes a cardiac stimulation device including a pulse generator that delivers defibrillation pulses between any combination of the defibrillation electrodes and pacing pulses to any one of the pacing electrodes and a sensing circuit that senses cardiac electrical activity with any one of the pacing electrodes.

20 Claims, 5 Drawing Sheets

U.S. PATENT DOCUMENTS

| | | | |
|---|---|---|---|
| 6,006,131 A | 12/1999 | Cooper et al. | 607/5 |
| 6,041,256 A | 3/2000 | Michel | 607/5 |
| 6,055,457 A | 4/2000 | Bonner | 607/126 |
| 6,067,471 A | 5/2000 | Warren | 607/5 |
| 6,070,100 A | 5/2000 | Bakels et al. | 607/9 |
| 6,070,101 A | 5/2000 | Struble et al. | 607/9 |
| 6,070,104 A | 5/2000 | Hine et al. | 607/123 |
| 6,081,748 A | 6/2000 | Struble et al. | 607/9 |
| 6,122,545 A | 9/2000 | Struble et al. | 607/9 |
| 6,169,921 B1 * | 1/2001 | KenKnight et al. | 607/4 |
| 6,205,357 B1 | 3/2001 | Ideker et al. | 607/14 |
| 6,249,700 B1 * | 6/2001 | Alt | 607/4 |
| 6,249,709 B1 | 6/2001 | Conger et al. | 607/122 |
| 6,266,563 B1 * | 7/2001 | KenKnight et al. | 607/5 |
| 6,339,724 B1 * | 1/2002 | Thong | 607/28 |
| 6,434,428 B1 * | 8/2002 | Sloman et al. | 607/28 |
| 6,434,430 B2 | 8/2002 | Borgersen et al. | 607/122 |
| 6,456,881 B1 * | 9/2002 | Bornzin et al. | 607/27 |
| 6,490,486 B1 | 12/2002 | Bradley | 607/28 |
| 6,490,489 B2 | 12/2002 | Bornzin et al. | 607/122 |
| 6,493,583 B1 | 12/2002 | Levine et al. | 607/9 |
| 6,587,720 B2 | 7/2003 | Hsu et al. | 607/4 |
| 2002/0103507 A1 | 8/2002 | Helland | 607/5 |
| 2003/0023271 A1 | 1/2003 | Hsu et al. | 607/4 |

\* cited by examiner

TWO LEAD UNIVERSAL DEFIBRILLATION, PACING AND SENSING SYSTEM

CROSS-REFERENCE TO RELATED APPLICATIONS

This application is related to copending, commonly-assigned U.S. patent applications: Ser. No. 09/910,154, filed Jul. 19, 2001, titled TWO LEAD UNIVERSAL DEFIBRILLATION SYSTEM; Ser. No. 09/944,678, filed Aug. 31, 2001, titled IMPLANTABLE CARDIAC LEAD FOR SHOCKING, PACING, AND SENSING WITHIN THE LEFT HEART AND SYSTEM; Ser. No. 09/945,415 filed Aug. 31, 2001, titled CORONARY SINUS LEAD FOR STIMULATING AND SENSING IN THE RIGHT AND LEFT HEART AND SYSTEM; Ser. No. 09/944,683, filed Aug. 31, 2001, titled CORONARY SINUS CARDIAC LEAD FOR STIMULATING AND SENSING THE ATRIA OF THE RIGHT AND LEFT HEART AND SYSTEM; Ser. No. 09/945,079, filed Aug. 31, 2001, titled THREE LEAD UNIVERSAL PACING AND SHOCKING SYSTEM; and Ser. No. 09/945,417, filed Aug. 31, 2001, titled TWO LEAD CARDIAC STIMULATION SYSTEM THAT PACES ALL FOUR CHAMBERS OF A HEART.

FIELD OF THE INVENTION

The present invention generally relates to an implantable cardiac stimulation system and more particularly to a two lead universal cardiac stimulation system capable of sensing and applying pacing and defibrillating pulses to all four chambers of the heart. The present invention is further directed to such a system which includes a lead implantable in the coronary sinus region of the heart.

BACKGROUND OF THE INVENTION

Implantable cardiac stimulation devices are well known in the art. Such devices may include, for example, implantable cardiac pacemakers and defibrillators. The devices are generally implanted in a pectoral region of the chest beneath the skin of a patient within what is known as a subcutaneous pocket. The implantable devices generally function in association with one or more electrode carrying leads which are implanted within the heart. The electrodes are usually positioned within the right side of the heart, either within the right ventricle or right atrium, or both, for making electrical contact with their respective heart chamber. Conductors within the leads and a proximal connector carried by the leads couple the electrodes to the device to enable the device to sense cardiac electrical activity and deliver the desired therapy.

Traditionally, therapy delivery had been limited to the venous, or right side of the heart. The reason for this is that implanted electrodes can cause blood clot formation in some patients. If a blood clot were released arterially from the left heart, as for example the left ventricle, it could pass directly to the brain potentially resulting in a paralyzing or fatal stroke. However, a blood clot released from the right heart, as from the right ventricle, would pass into the lungs where the filtering action of the lungs would prevent a fatal or debilitating embolism in the brain.

Recently, new lead structures and methods have been proposed and even practiced for delivering cardiac rhythm management therapy to the left heart. These lead structures and methods avoid direct electrode placement within the left atrium and left ventricle of the heart by lead implantation within the coronary sinus region of the heart. As used herein, the phrase "coronary sinus region" refers to the venous vasculature of the left ventricle, including any portions of the coronary sinus, great cardiac vein, left marginal vein, left posterior ventricular vein, middle cardiac vein, and/or small cardiac vein or any other cardiac vein accessible by the coronary sinus.

It has been demonstrated that electrodes placed in the coronary sinus region of the heart may be used for left atrial pacing, left ventricular pacing, or cardioversion and defibrillation. These advancements enable implantable cardiac stimulation devices to address the needs of a patient population with left ventricular dysfunction and/or congestive heart failure which would benefit from left heart side pacing, either alone or in conjunction with right heart side pacing (bi-chamber pacing), and/or defibrillation.

Universal pacing and/or defibrillation systems capable of pacing and/or defibrillating all of the chambers of the right and left heart would of course require numerous pacing and/or defibrillation electrodes to be employed within the heart and its coronary venous system. Providing the numerous electrodes to implement such universal heart stimulation systems would in turn require an inordinate number of leads if currently available right and left heart leads were employed. This would result in unduly long implant procedures and possibly more leads than the human anatomy is able to accommodate. The number of leads required may also make it difficult to accurately locate each electrode at its most efficacious position within the heart.

Hence, there is a need in the art for new and improved right and left heart leads and lead configurations which provide efficient left heart access and integrated right and left heart therapies. Electrode placement on the leads should enable effective therapy and electrode selection to accommodate differences in heart physiology from one patient to another. Universal pacing and defibrillation systems that would result from the new and improved leads and lead configurations could provide significant improved therapies. Coordinated right heart and left heart pacing therapies would be made possible. Further, improved defibrillation therapies would also be made possible. The therapies could provide improved electrode configuration selection for improved defibrillation energy distribution within the heart or support improved sequential defibrillation pulse techniques. The present invention is directed to left heart leads and right and left heart lead configurations which address the above mentioned needs.

SUMMARY OF THE INVENTION

The invention provides an implantable cardiac stimulation system capable of sensing electrical activity of the heart in all four chambers of the heart and delivering pacing and defibrillation pulses to all four chambers of the heart. The system includes a lead system consisting of first and second leads. The first lead includes a right ventricular pacing electrode for placement in the right ventricle, a right ventricular defibrillation electrode for placement in the right ventricle, and a right atrial defibrillation lead for placement in the right atrium and/or the superior vena cava of the heart. The second lead includes a left ventricular pacing electrode for placement in electrical contact with the left ventricle, a left ventricular defibrillation electrode for placement in electrical contact with the left ventricle, a left atrial pacing electrode for placement in electrical contact with the left atrium, and a left atrial defibrillation electrode for placement in electrical contact with the left atrium of the heart, and a right atrial pacing electrode carried by one of the first and second leads for placement in the right atrium. The system further includes a cardiac stimulation device including a pulse generator that delivers defibrillation pulses between any combination of the defibrillation electrodes and pacing pulses to any one of the pacing electrodes and a sensing circuit that senses electrical activity of the heart with any one of the pacing electrodes.

In accordance with further aspects of the invention, the right ventricular defibrillation electrode, the right atrial defibrillation electrode, the left ventricular defibrillation electrode and the left atrial defibrillation electrode may be coil electrodes. Still further, the cardiac stimulation device may include a conductive case which may serve as a return electrode wherein the pulse generator of the cardiac stimulation device delivers defibrillation pulses between any combination of the defibrillation electrodes and the conductive case or pacing pulses between any one of the pacing electrodes and the conductive case.

The second lead is preferably implantable within the coronary sinus of the heart with the left ventricular pacing electrode, the left ventricular defibrillation electrode, the left atrial pacing electrode, and the left atrial defibrillation electrode spaced apart on the second lead so that when the left ventricular pacing electrode and the left ventricular defibrillation electrode are adjacent to the left ventricle within the coronary sinus of the heart, the left atrial pacing electrode and the left atrial defibrillation electrode are adjacent to the left atrium within the coronary sinus of the heart.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Exemplary Embodiment of the Invention

Figure 1:
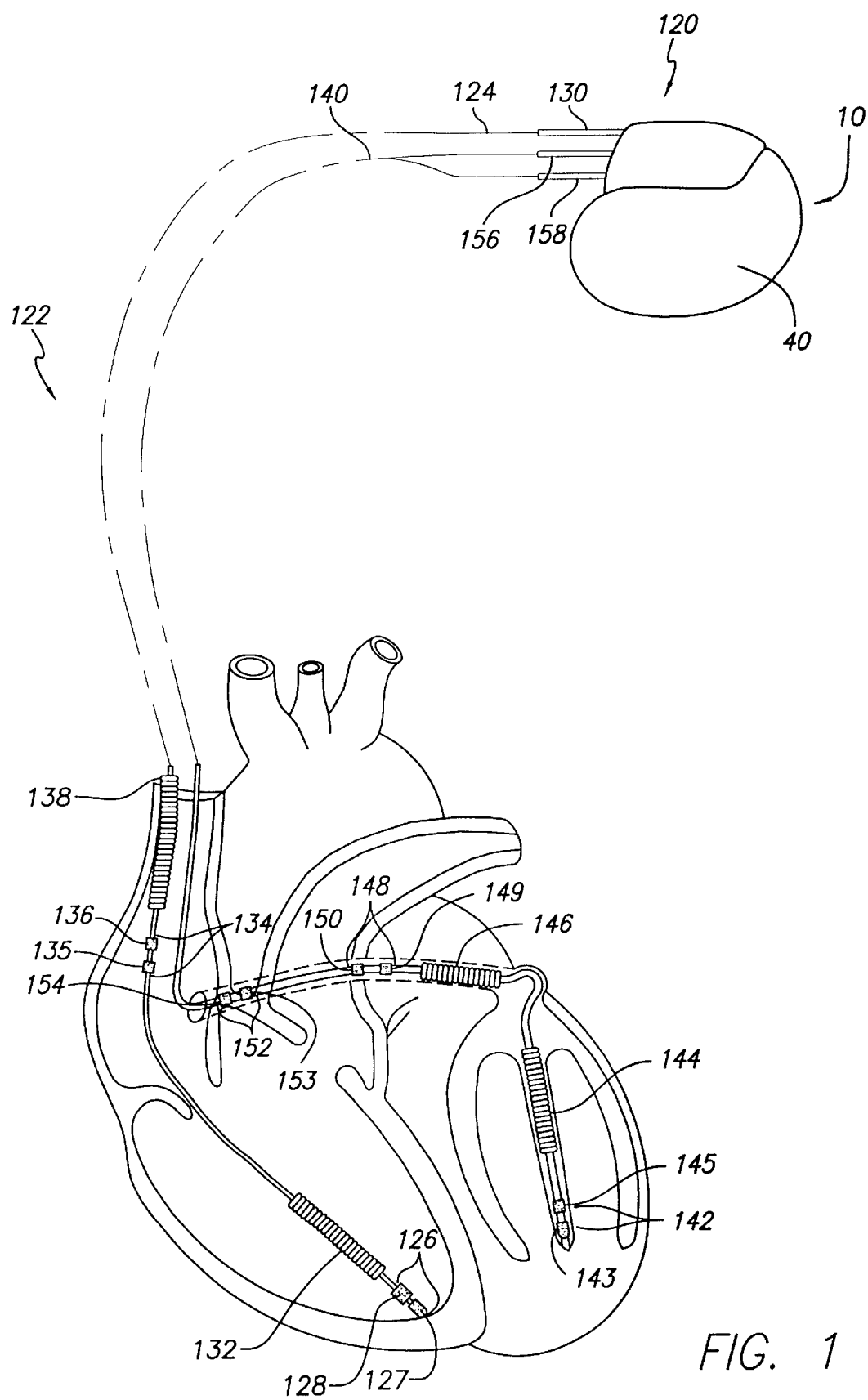
FIG. 1 is a simplified diagram illustrating a two lead implantable universal cardiac stimulation system embodying the present invention capable of sensing and delivering both pacing and defibrillation therapy to all four chambers of the heart.

FIG. 1 shows a two lead implantable cardiac stimulation system 120 embodying the present invention. The system includes an implantable cardiac stimulation device 10 and a lead system 122 consisting of two leads, lead 124 and lead 140.

The lead 124 is configured for implant in the right heart. The lead 124 includes, from its distal end towards its proximal end, a right ventricular bipolar pacing and sensing electrode pair 126, a right ventricular defibrillation coil electrode 132, a right atrial bipolar sensing and pacing electrode pair 134, and a right atrial defibrillation coil electrode 138. The lead 124 is configured for implant in the right heart by being advanced through the superior vena cava, into the right atrium, and then into the right ventricle as illustrated.

The right ventricular bipolar electrode pair 126 includes a right ventricular tip electrode 127 and a right ventricular bipole electrode 128. The right atrial bipolar electrode pair 134 includes electrodes 135 and 136. The electrodes are spaced apart on the lead 124 such that when the right ventricular bipolar electrode pair 126 and the right ventricular defibrillation coil electrode 132 are within the apex of the right ventricle, the right atrial bipolar electrode pair 134 is within the right atrium and the right atrial defibrillation coil electrode 138 is within the right atrium and/or the superior vena cava.

Figure 2:
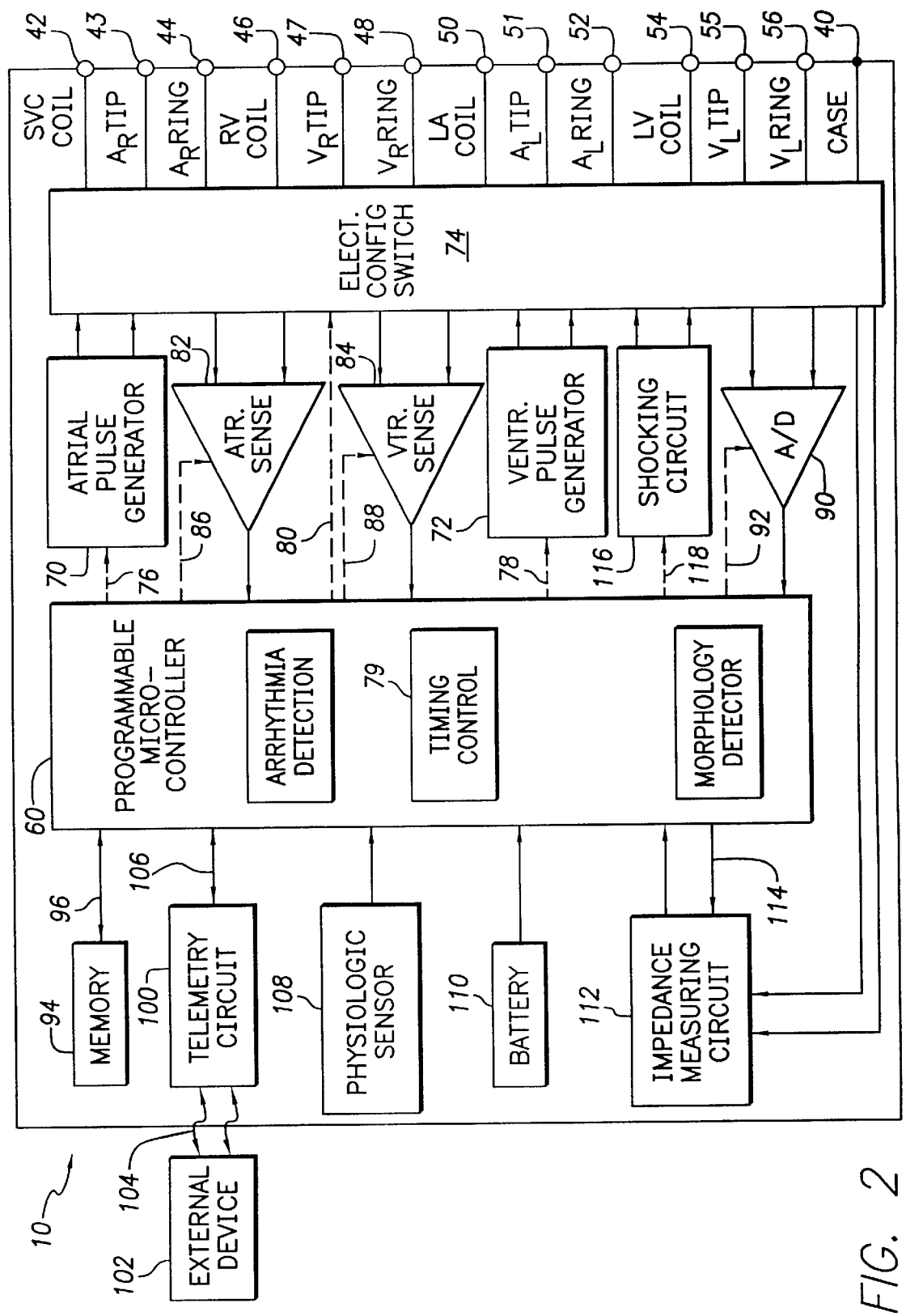
FIG. 2 is a functional block diagram of a multi-chamber implantable stimulation device which may be employed in the system of FIG. 1 which can provide cardioversion, defibrillation and pacing stimulation for all four chambers of the heart.

The lead 124 further includes a proximal connector 130 which couples the electrodes of lead 124 to the internal circuitry of the device 10. With reference to FIG. 2, the connector 130 preferably connects the right ventricular tip electrode 127 to the right ventricular tip terminal 47, the right ventricular bipole electrode 128 to the right ventricular ring terminal 48, the right ventricular defibrillation coil electrode 132 to the right ventricular coil terminal 46, the right atrial pacing and sensing electrode 135 to the right atrial tip terminal 43, the right atrial sensing and pacing electrode 136 to the right atrial ring terminal 44, and the right atrial defibrillation coil electrode 138 to the SVC coil terminal 42 of the device 10.

Lead 140 is configured for implant in the left heart. It includes, from its distal end towards its proximal end, a left ventricular bipolar sensing and pacing electrode pair 142, a left ventricular defibrillation coil electrode 144, a left atrial defibrillation coil electrode 146, and a left atrial bipolar sensing and pacing electrode pair 148. As further illustrated in FIG. 1, the lead 140 may further include a right atrial bipolar sensing and pacing electrode pair 152. The right atrial bipolar sensing and pacing electrode pair 152 may be optionally included on lead 140 if the right atrial bipolar sensing and pacing electrode pair 134 are omitted from lead 124.

The left ventricular bipolar sensing and pacing electrode pair 142 includes a left ventricular tip electrode 143 and a left ventricular bipole electrode 145. The left atrial bipolar sensing and pacing electrode pair 148 includes electrode 149 and electrode 150. The electrodes are spaced apart on the lead 140 such that when the left ventricular bipolar sensing and pacing electrode pair 142 are in electrical contact with and adjacent to the left ventricle within the coronary sinus, the left ventricular defibrillation coil electrode 144 is also in electrical contact with and adjacent to the left ventricle within the coronary sinus, the left atrial defibrillation coil electrode 146 is in electrical contact with and adjacent to the left atrium within the coronary sinus, and the left atrial bipolar sensing and pacing electrode pair 148 are also in electrical contact with and adjacent to the left atrium within the coronary sinus.

The right atrial bipolar sensing and pacing electrode pair 152 includes electrodes 153 and 154. As is traditional with bipolar electrode pairs, the electrodes 153 and 154 are closely spaced apart. The electrodes 153 and 154 are further located on the lead 140 so that with the lead 140 positioned in the left heart as described above, the electrodes 153 and 154 are in electrical contact with and adjacent to the right atrium within the coronary sinus. More specifically, the electrode 154 is adjacent the ostium of the coronary sinus within the coronary sinus. Such placement of electrodes 153 and 154 permit the bipolar electrode pair 152 to sense heart activity of the right atrium and provide the right atrium with pacing stimulation pulses.

As illustrated, the electrodes are preferably coil electrodes. However, other types of electrodes, such as plural interconnected ring electrodes, as are known in the art may also be employed.

As further illustrated in FIG. 1, the lead 140 is bifurcated at its proximal end and includes proximal connectors 156 and 158. The proximal connectors 156 and 158 coupled the electrodes of lead 140 to the internal circuitry of the device 10. With reference to FIG. 2, the connectors 156 and 158 preferably couple the left ventricular tip electrode 143 to the left ventricular tip terminal 55, the left ventricular bipole electrode 145 to the left ventricular ring terminal 56, the left ventricular defibrillation coil electrode 144 to the left ventricular coil terminal 54, the left atrial defibrillation coil electrode 146 to the left atrial coil terminal 50, the left atrial sensing and pacing electrode 149 to the left atrial tip terminal 51, and the left atrial bipole electrode 150 to the left atrial ring terminal 52 of the device 10. Where the right atrial bipolar electrode pair 152 is provided on the lead 140, the right atrial sensing and pacing electrode 153 is coupled to the right atrial tip terminal 43 and the right atrial bipole electrode 154 is coupled to the right atrial ring terminal 44 of the device.

In accordance with the present invention, the lead system 122 provides a lead system consisting of two leads which enables universal pacing, sensing, and defibrillation of the heart. More specifically, with respect to sensing, any one of the bipolar sensing and pacing electrode pairs may be utilized for sensing electrical activity of their corresponding chamber. With respect to pacing, once again, any one of the bipolar sensing and pacing electrode pairs may be utilized for providing pacing stimulation to their corresponding chamber. Lastly, any one or any combination of the defibrillation coil electrodes 132, 144, 138, and 146 may be employed for defibrillating the heart. Further, the device includes a conductive case 40 which may additionally be employed as a return stimulation electrode for unipolar pacing or heart defibrillation.

From the foregoing, it can be appreciated that the cardiac stimulation system 120 provides the physician with numerous electrode configuration therapy alternatives. As a result, the universal pacing, sensing, and shocking system of FIG. 1 may be programmed to meet the particular needs and physiology of a patient.

An Exemplary Cardiac Stimulation Device

As illustrated in FIG. 2, a simplified block diagram is shown of a multi-chamber implantable stimulation device 10 which may be employed to advantage in the system of FIG. 1 or with any of the other lead systems described herein. The device is capable of treating arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as a return stimulation electrode for all "unipolar" pacing modes. The housing 40 may further be used as a return electrode alone or in combination with one or more of the coil electrodes for shocking purposes. The housing 40 further includes a connector (not shown) having a plurality of terminals, 42, 43, 44, 46, 47, 48, 50, 51, 52, 54, 55, and 56 (shown schematically and, for convenience, the names of the electrodes to which they may be connected as appropriate are shown next to the terminals).

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses. The pacing stimulation pulses are made available as required at terminal 43 ($A_R$ TIP), terminal 44 ($A_R$ RING), terminal 47 ($V_R$ TIP), terminal 48 ($V_R$ RING), terminal 51 ($A_L$ TIP), terminal 52 ($A_L$ RING), terminal 55 ($V_L$ TIP) and terminal 56 ($V_L$ RING). The device is thus capable of providing stimulation pacing pulses for use in each of the four chambers of the heart. The atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to appropriate ones of the terminals for connection to corresponding lead electrodes for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 may be coupled to any combination of the terminals 424–44, 46–48, 50–52, and 54–56 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

The stimulation device 10 may further include a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. The type of sensor used is not critical to the present invention and is shown only for completeness.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown for example in FIG. 1, selected from the left atrial coil electrode, the left ventricular coil electrode, the SVC coil electrode, and the right ventricular coil electrode. As noted above, the housing 40 may act as a return electrode in combination with any one of the electrodes, or any combination of the electrodes for example, as part of a split electrical vector using the SVC coil electrode or the left atrial coil electrode (i.e., using the RV coil electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Further Embodiments of the Invention

Figure 3:
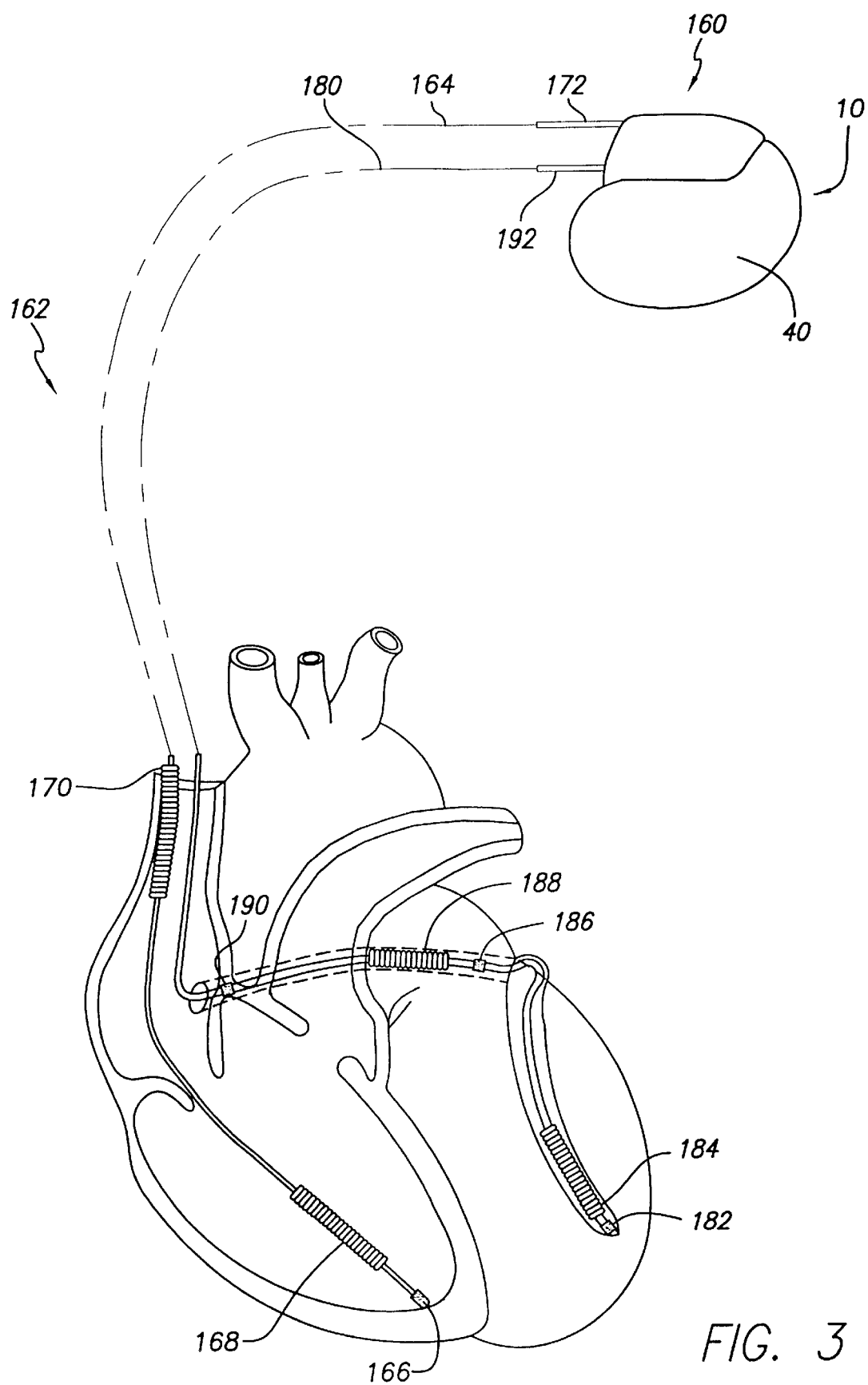
FIG. 3 is a further simplified diagram illustrating another two lead implantable universal cardiac stimulation system embodying the present invention capable of providing defibrillation and pacing therapy to all four chambers of the heart.

FIG. 3 illustrates another cardiac stimulation system 160 embodying the present invention. The system 160 includes the device 10 and a lead system 162. In accordance with the present invention, the lead system 162 consists of two leads, lead 164 and lead 180.

Lead 164 is configured for implant in the right heart. It includes a right ventricular tip electrode 166, a right ventricular defibrillation coil electrode 168, and a right atrial defibrillation coil electrode 170. The electrodes are spaced apart on the lead 164 such that when the right ventricular tip electrode 166 is within the apex of the right ventricle, the right ventricular defibrillation coil electrode 168 is within the right ventricle and the right atrial defibrillation coil electrode 170 is within the right atrium and/or the superior vena cava of the heart.

The lead 164 further includes a proximal connector 172 which couples the electrodes of lead 164 to the internal circuitry of the device 10. With reference to FIG. 2, the proximal connector 172 preferably couples the right ventricular tip electrode 166 to the right ventricular tip terminal 47, the right ventricular defibrillation coil electrode 168 to the right ventricular coil terminal 46, and the right atrial defibrillation coil electrode 170 to the SVC coil terminal 42.

The lead 180 is configured for implant in the left heart. It includes a left ventricular tip electrode 182, a left ventricular defibrillation coil electrode 184, a left atrial sensing and pacing electrode 186, a left atrial defibrillation coil electrode 188, and a right atrial sensing and pacing electrode 190. The electrodes are spaced apart on the lead 180 such that when the left ventricular tip electrode 182 is in electrical contact with and adjacent to the left ventricle within the coronary sinus as illustrated, the left ventricular defibrillation coil electrode 184 is in electrical contact with and adjacent to the left ventricle within the coronary sinus, the left atrial sensing and pacing electrode 186 is in electrical contact with and adjacent to the left atrium within the coronary sinus, the left atrial defibrillation coil electrode 188 is in electrical contact with and adjacent to the left atrium within the coronary sinus, and the right atrial sensing and pacing electrode 190 is in electrical contact with and adjacent to the right atrium within the coronary sinus. More particularly, with respect to electrode 190, it is preferably positioned on the lead 180 such that when the lead is positioned within the left heart as illustrated and described above, the electrode 190 is adjacent the ostium of the coronary sinus within the coronary sinus.

The lead 180 further includes a proximal connector 192. The connector 192 couples the electrodes of the lead 180 to the internal circuitry of the device 10. With reference to FIG. 2, the connector 192 couples the left ventricular tip electrode 182 to the left ventricular tip terminal 55, the left ventricular defibrillation coil electrode 184 to the left ventricular coil terminal 54, the left atrial sensing and pacing electrode 186 to the left atrial tip terminal 47, the left atrial defibrillation coil electrode 188 to the left atrial coil terminal 50, and a right atrial sensing and pacing electrode 190 to the right atrial tip terminal 43.

In accordance with the present invention, any one or combination of the defibrillation coil electrodes 168, 170, 184, and 188 may be utilized for defibrillating the heart. In addition, the conductive case 40 of the device 10 may be utilized as a return electrode during defibrillation of the heart.

In addition, the lead system 162 provides for both sensing and pacing in each of the chambers of the heart. The right ventricular tip electrode 166 may be used for sensing in and pacing the right ventricle in a unipolar mode using the conductive case 40 of the device 10 as a return electrode. The right ventricular tip electrode 166 may alternatively be used for sensing or pacing in a bipolar mode utilizing the right ventricular defibrillation coil electrode 168 as a bipole electrode. Right atrial sensing and pacing may be carried out utilizing the right atrial sensing and pacing electrode 190 in a unipolar mode with the case 40 of the device 10. Left ventricular sensing and pacing may be carried out by utilizing the left ventricular tip electrode 182 either in a unipolar mode with the case 40 of device 10 or in a bipolar mode utilizing the left ventricular defibrillation coil electrode 184 as a bipole electrode. Lastly, left atrial sensing and pacing may be carried out by using the left atrial sensing and pacing electrode 166 in a unipolar mode with the conductive case 40 of the device 10 or in a bipolar mode utilizing the left atrial defibrillation coil electrode 188 as a bipole electrode.

Figure 4:
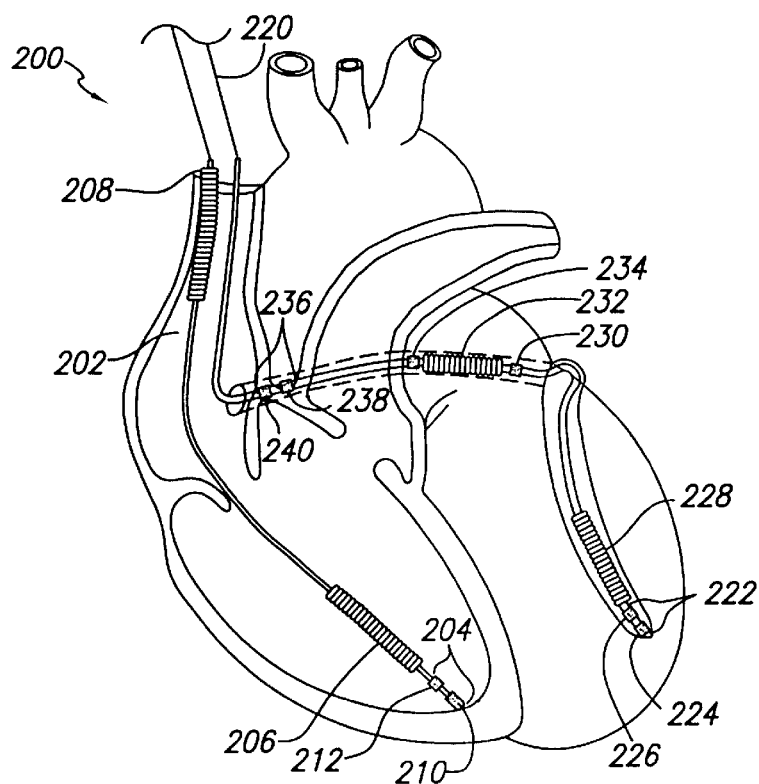
FIG. 4 is a simplified diagram illustrating a further two lead implantable lead system embodying the present invention capable of delivering both pacing and defibrillation therapy to all four chambers of the heart.

FIG. 4 shows another lead system 200 embodying the present invention. In accordance with the present invention, the lead system 200 consists of two leads, lead 202 and lead 220.

The lead 202 is configured for implant in the right heart. It includes a right ventricular bipolar sensing and pacing electrode pair 204, a right ventricular defibrillation coil electrode 206, and a right atrial defibrillation coil electrode 208. The right ventricular bipolar sensing and pacing electrode pair includes a right ventricular tip electrode 210 and a right ventricular bipole electrode 212. The electrodes are spaced apart on the lead 202 such that when the right ventricular bipolar sensing and pacing electrode pair 204 are in the apex of the right ventricle, the right ventricular defibrillation coil electrode 206 is within the right ventricle and the right atrial defibrillation coil electrode 208 is within the superior vena cava and/or the right atrium.

The lead 220 is configured for implant in the left heart. It includes a left ventricular bipolar sensing and pacing electrode pair 222, a left ventricular defibrillation coil electrode 228, a left atrial distal sensing and pacing electrode 230, a left atrial defibrillation coil electrode 232, and a left atrial sensing and pacing proximal electrode 234. The lead 220 further includes a right atrial bipolar sensing and pacing electrode pair 236. The left ventricular bipolar sensing and pacing electrode pair 222 includes a left ventricular tip electrode 224, and a left ventricular bipole electrode 226. The right atrial bipolar sensing and pacing electrode pair 236 includes an electrode 238 and an electrode 240. The electrodes are spaced apart on the lead 220 so that when the left ventricular sensing and pacing bipolar electrode pair 222 are in electrical contact with and adjacent the left ventricle within the coronary sinus as illustrated, the left ventricular defibrillation coil electrode 228 is in electrical contact with and adjacent the left ventricle within the coronary sinus, the left atrial electrodes 230, 232, and 234 are in electrical contact with and adjacent the left atrium within the coronary sinus, and the right atrial bipolar sensing and pacing electrode pair 236 is in electrical contact with and adjacent the right atrium within the coronary sinus. More particularly, the right atrial sensing and pacing electrode 240 is adjacent the ostium of the coronary sinus within the coronary sinus.

As in the previous embodiments, the electrodes of the lead system 200 may be coupled to the internal circuitry of the device 10 by proximal connectors (not shown) carried by the leads 202 and 220. When coupled to the internal circuitry of the device 10, and with reference to FIG. 2, the right ventricular tip electrode 210 is coupled to the right ventricular tip terminal 47, the right ventricular bipole electrode 212 is coupled to the right ventricular ring 48, the right ventricular defibrillation coil electrode 206 is coupled to the right ventricular coil terminal 46, and the right atrial defibrillation coil electrode 208 is coupled to the SVC coil terminal 42. Further, the left ventricular tip electrode 224 is coupled to the left ventricular tip terminal 55, the left ventricular bipole electrode 226 is coupled to the left ventricular ring terminal 56, the left ventricular defibrillation coil electrode 228 is coupled to the left ventricular coil terminal 54, the left atrial sensing and pacing electrode 230 is coupled to the left atrial tip terminal 51, the left atrial defibrillation coil electrode 232 is coupled to the left atrial coil terminal 50, the left atrial sensing and pacing electrode 234 is coupled to the left atrial ring terminal 52, the right atrial pacing and sensing electrode 238 is coupled to the right atrial tip terminal 43, and the right atrial pacing and sensing electrode 240 is coupled to the right atrial ring terminal 44.

The lead system 200 of FIG. 4 provides universal defibrillation therapy to the heart. Any one of the defibrillation coil electrodes or any combination of these electrodes may be utilized for defibrillating the heart. In addition, the conductive case 40 of the device 10 may further be utilized as a return electrode during defibrillation.

For sensing and pacing, the lead system 200 again provides a universal system wherein all four chambers of the heart may be separately monitored and provided with pacing therapy. For example, each of the bipolar electrode pairs 222, 204, and 236 may be utilized for sensing in and pacing its corresponding heart chamber. With respect to the left atrium, bipolar sensing and pacing may be carried out by utilizing either a bipolar pair including the left atrial sensing and pacing electrode 230 with the left atrial defibrillation coil electrode 232 or the left atrial sensing and pacing electrode 234 with the left atrial defibrillation coil electrode 232.

Figure 5:
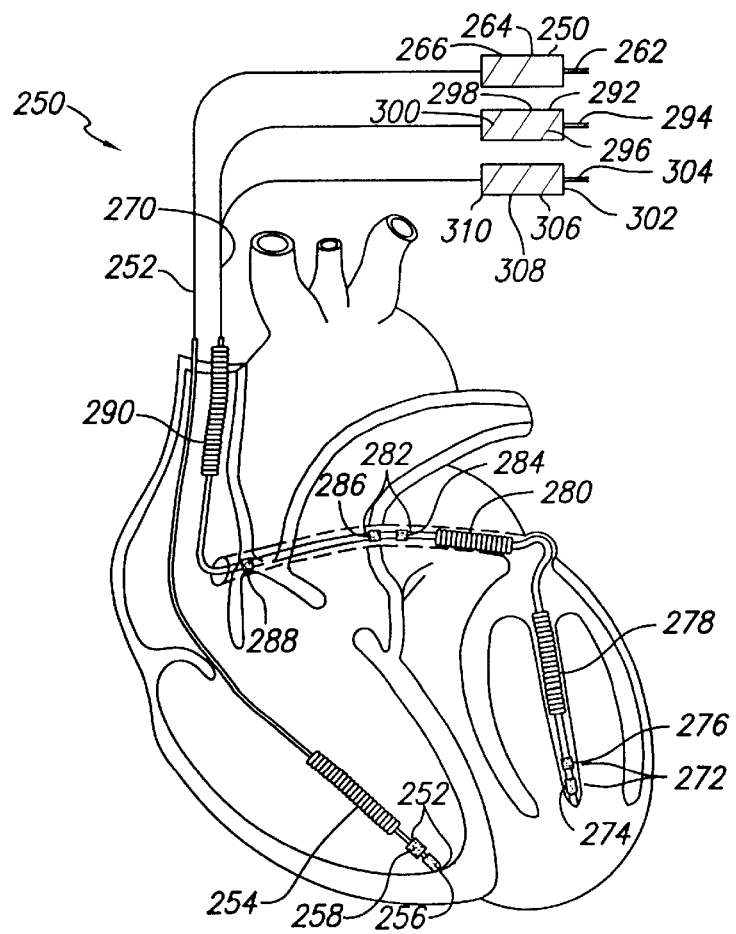
FIG. 5 is a further simplified diagram illustrating another two lead implantable lead system embodying the present invention capable of providing defibrillation and pacing therapy to all four chambers of the heart.

Referring now to FIG. 5, it illustrates a further lead system 250 embodying the present invention. Again, the lead system 250 consists of two leads, 252 and 270 which provide universal defibrillation, sensing, and pacing in all four chambers of the heart. The lead 252 is configured for implant in the right heart. It includes a right ventricular bipolar sensing and pacing electrode pair 252 and a right ventricular defibrillation coil electrode 254. The bipolar electrode pair 252 includes a right ventricular tip electrode 256 and a right ventricular bipole electrode 258.

The lead 270 is configured for implant in the left heart. It includes a left ventricular bipolar sensing and pacing electrode pair 272, a left ventricular defibrillation coil electrode 278, a left atrial defibrillation coil electrode 280, a left atrial bipolar sensing and pacing electrode pair 282, a right atrial sensing and pacing electrode 288, and a right atrial defibrillation coil electrode 290. The left ventricular bipolar electrode pair 272 includes a left ventricular tip electrode 274 and a left ventricular bipole electrode 276. The right atrial bipolar electrode pair includes a distal left atrial sensing and pacing electrode 284 and a left atrial proximal sensing and pacing electrode 286.

The electrodes are spaced apart on the lead 270 so that when the electrodes 274 and 276 of the left ventricular bipolar electrode pair 272 are in electrical contact with and adjacent the left ventricle within the coronary sinus as illustrated, the left ventricular defibrillation coil electrode 278 is in electrical contact with and adjacent the left ventricle within the coronary sinus, the left atrial defibrillation coil electrode is in electrical contact with and adjacent the left atrium within the coronary sinus, the left atrial bipolar sensing and pacing electrode pair 282 is in electrical contact with and adjacent the left atrium within the coronary sinus, the right atrial sensing and pacing electrode 288 is in electrical contact with and adjacent the right atrium, and the right atrial defibrillation coil electrode 290 is within the superior vena cava and/or the right atrium. With respect to electrode 288, it is positioned on the lead so that it is preferably within the coronary sinus and immediately adjacent the ostium of the coronary sinus.

The electrodes of the lead system 250 may be coupled to the internal circuitry of the implantable cardiac stimulation device 10. To that end, the lead 252 includes a proximal connector 260 having a connector pin 262 and connector contacts 264 and 266 in a manner known in the art. The lead 270 is bifurcated at its proximal end and includes proximal connectors 292 and proximal connector 302. Connector 292 has a connector pin 294 and contacts 298 and 300. Similarly, connector 302 has a connector pin 304 and contacts 306, 308, and 310.

With reference to FIG. 2, when connector 260 connects the electrodes of lead 252 to the device 10, the right ventricular tip electrode 256 is coupled to the right ventricular tip terminal 47, the right ventricular ring electrode 258 is coupled to the right ventricular ring terminal 48, and the right ventricular coil electrode is coupled to the right ventricular coil terminal 46. When the electrodes of lead 270 are coupled to the device 10 by the connectors 292 and 302, the left ventricular tip electrode 274 is connected to the left ventricular tip terminal 55, the left ventricular ring electrode 276 is coupled to the left ventricular ring terminal 56, the left ventricular defibrillation coil electrode is coupled to the left ventricular coil terminal 54, the left atrial defibrillation coil electrode 280 is coupled to the left atrial coil terminal 50, the left atrial distal sensing and pacing electrode 284 is coupled to the left atrial tip terminal, the left atrial sensing and pacing proximal electrode 286 is coupled to the left atrial ring terminal 52, the right atrial sensing and pacing electrode 288 is coupled to the right atrial tip terminal 43, and the right atrial defibrillation 290 is coupled to the SVC coil terminal 42.

Any one of the defibrillation coil electrodes or any combination of the defibrillation coil electrodes may be utilized for defibrillating either the atria or ventricles of the heart. Again, the conductive case of the device may be utilized as a return electrode during defibrillation. Also, the electrical activity of the heart within all four chambers may be sensed and pacing therapy may be applied to each of the chambers of the heart. Preferably, sensing within and pacing of the right ventricle, the left ventricle, and the left atrium is performed utilizing the bipolar electrode pairs 252, 272, and 282, respectively. With respect to the right atrium, the electrical activity of the right atrium may be sensed and pacing therapy may be applied utilizing the right atrial sensing and pacing electrode 288 in a unipolar mode along with the conductive case of the device as a return electrode. Alternatively, bipolar sensing and pacing may be accomplished utilizing the electrode 288 with the right atrial defibrillation coil electrode 290 as a bipolar pair. Again, unipolar sensing or pacing may be carried out with any one of the sensing and pacing electrodes while utilizing the conductive case of the device as a return electrode.

Figure 6:
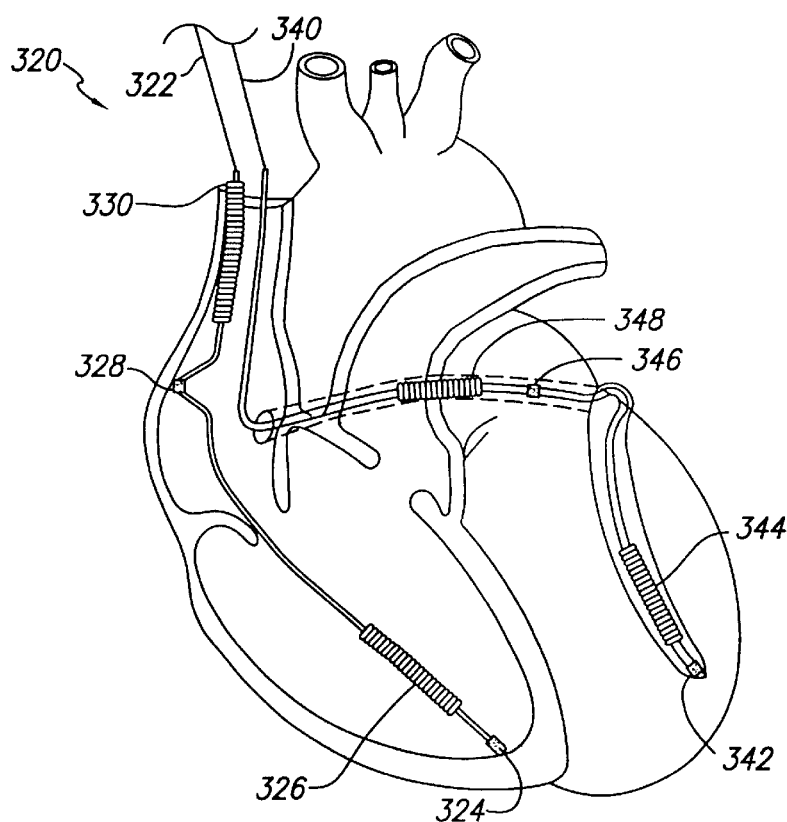
FIG. 6 is another simplified diagram illustrating a further two lead implantable lead system embodying the present invention capable of delivering both pacing and defibrillation therapy to all four chambers of the heart.

Referring now to FIG. 6, it illustrates another lead system 320 embodying the present invention. Here again, the lead system 320 consists of two leads, lead 322 and 340.

Lead 322 is configured for implant in the right heart. It includes a right ventricular tip electrode 324, a right ventricular defibrillation coil electrode 326, a right atrial sensing and pacing electrode 328, and a right atrial defibrillation coil electrode 330. The electrodes are spaced apart such that when the right ventricular tip electrode 324 is within the apex of the right ventricle as illustrated, the right ventricular defibrillation coil electrode 326 is within the right ventricle, the right atrial sensing and pacing electrode 328 is within the right atrium, and the right atrial defibrillation coil electrode 330 is within the superior vena cava and/or the right atrium of the heart. As will be noticed in the figure, the lead 322 is further configured such that the right atrial pacing and sensing electrode 328 is in contact with the right anterior lateral wall of the right atrium.

The lead 340 is configured for implant in the left heart. It includes a left ventricular tip electrode 342, a left ventricular defibrillation coil electrode 344, a left atrial sensing and pacing electrode 346, and a left atrial defibrillation coil electrode 348. The electrodes are spaced apart on the lead 340 such that when the left ventricular tip electrode 342 is in electrical contact with and adjacent the left ventricle within the coronary sinus as illustrated, the left ventricular defibrillation coil electrode 344 is in electrical contact with and adjacent the left ventricle, the left atrial sensing and pacing electrode 346 is in electrical contact and adjacent the left atrium, and the left atrial defibrillation coil electrode 348 is in electrical contact with and adjacent the left atrium, all of the electrodes being within the coronary sinus.

As in the previous embodiments, the electrodes of the leads 322 and 340 may be connected to the internal circuitry of the device 10 by proximal connectors (not shown) carried by the leads 322 and 340. With reference to FIG. 2, when lead 322 is connected to the device, the right ventricular tip electrode 324 is coupled to the right ventricular tip terminal 47, the right ventricular defibrillation coil electrode 326 is coupled to the right ventricular coil terminal 46, the right atrial sensing and pacing electrode 328 is coupled to the right atrial tip terminal 43, and the right atrial defibrillation coil electrode 330 is coupled to the SVC coil terminal 42. When the lead 340 is connected to the device, the left ventricular tip electrode 342 is coupled to the left ventricular tip terminal 55, the left ventricular defibrillation coil electrode 344 is coupled to the left ventricular coil terminal, the left atrial sensing and pacing electrode 346 is coupled to the left atrial tip terminal 51, and the left atrial defibrillation coil electrode 348 is coupled to the left atrial coil terminal 50.

With the lead system 320 of FIG. 6, defibrillation therapy may be applied to any one of the four chambers of the heart. The defibrillation therapy may be applied using any one of the electrodes or any combination of the electrodes. Again, the conductive case of the device may be used during defibrillation as a return electrode.

For sensing in the four chambers of the heart and providing pacing therapy to the four chambers of the heart, each of the sensing and pacing electrodes 328, 324, 342, and 346 may be utilized in a unipolar mode along with the conductive case of the device. Alternatively, each of these electrodes may be utilized in conjunction with its associated defibrillation coil electrode for providing bipolar sensing and pacing of its corresponding chamber.

Figure 7:
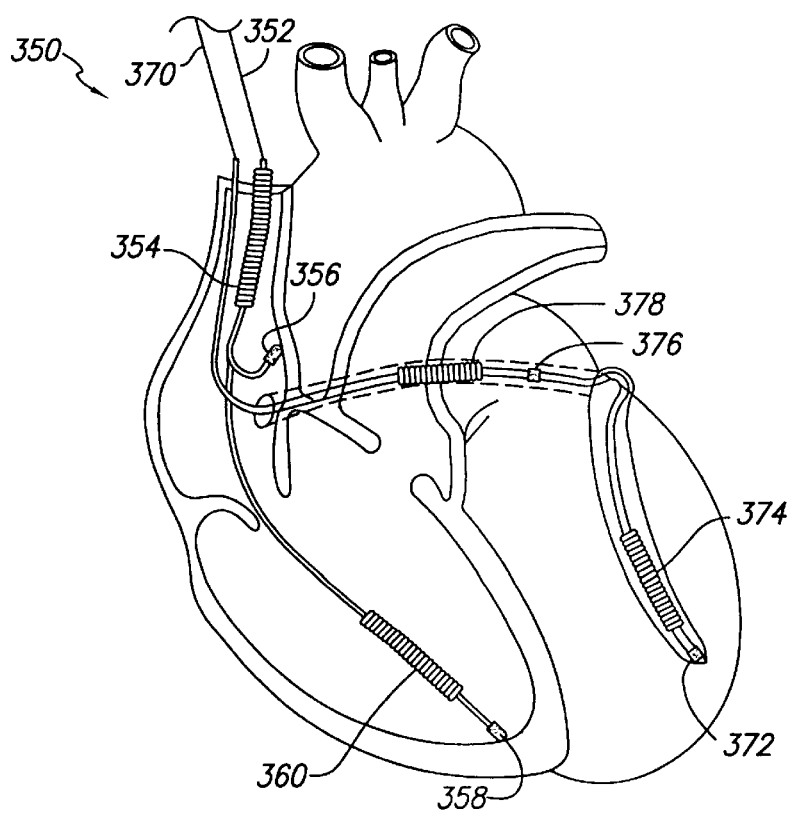
FIG. 7 is a further simplified diagram illustrating another two lead implantable lead system embodying the present invention capable of providing defibrillation and pacing therapy to all four chambers of the heart.

FIG. 7 shows a still further lead system 350 embodying the present invention. The lead system 350 consists of two leads, lead 352 and lead 370.

Lead 352 is configured for implant in the right heart. Lead 352 includes a right atrial defibrillation coil electrode 354 and is bifurcated having a first branch including a right atrial sensing and pacing electrode 356 and a second branch including a right ventricular tip electrode 358 and a right ventricular defibrillation coil electrode 360. The right atrial sensing and pacing electrode 356 preferably is of the type having a screw-in tip as is well known in the art. The electrodes are spaced apart on the lead 352 so that when the right ventricular tip electrode 358 is in the apex of the right ventricle as illustrated, the right ventricular defibrillation coil electrode 360 is in the right ventricle, the right atrial sensing and pacing electrode 356 is positioned for being secured to the wall of the right atrium, and the right atrial defibrillation coil electrode 354 is within the superior vena cava and/or the right atrium.

The lead 370 is configured for implant in the left heart. It includes a left ventricular tip electrode 372, a left ventricular defibrillation coil electrode 374, a left atrial sensing and pacing electrode 376, and a left atrial defibrillation coil electrode 378. The electrodes are spaced apart on the lead 370 such that when the left ventricular tip electrode 372 is in electrical contact with and adjacent the left ventricle within the coronary sinus, the left ventricular defibrillation coil electrode 374 is in electrical contact with and adjacent the left ventricle within the coronary sinus, the left atrial sensing and pacing electrode 376 is in electrical contact with and adjacent the left atrium within the coronary sinus, and the left atrial defibrillation coil electrode 378 is in electrical contact with and adjacent the left atrium within the coronary sinus.

Any one or combination of the defibrillation coil electrodes 354, 360, 374, and 378 may be utilized for defibrillating the heart. Again, during defibrillation, the conductive case of the device may be utilized as a return electrode. Any one of the sensing and pacing electrodes 356, 358, 372, and 376 may be employed in a unipolar mode with the conductive case of the device for sensing in or pacing its corresponding chamber. Also, as in the previous embodiment, each of the sensing and pacing electrodes 356, 358, 372, and 376 may be utilized in a bipolar mode with its corresponding defibrillation coil electrode 354, 360, 374, and 378, respectively, for sensing in and pacing the right atrium, right ventricle, left ventricle, and left atrium, respectively.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation system capable of sensing electrical activity of the heart in all four chambers of the heart and delivering pacing and defibrillation pulses to all four chambers of the heart, the system comprising:

a lead system consisting of first and second leads, the first lead including a right atrial pacing electrode for placement in the right atrium, a right ventricular pacing electrode for placement in the right ventricle, a right ventricular defibrillation electrode for placement in the right ventricle, and a right atrial defibrillation electrode for placement in the right atrium and/or the superior vena cava of the heart, the second lead including a right atrial bipolar pacing electrode for placement in electrical contact with the right atrium, a left ventricular pacing electrode for placement in electrical contact with the left ventricle, a left ventricular defibrillation electrode for placement in electrical contact with the left ventricle, a left atrial pacing electrode for placement in electrical contact with the left atrium, and a left atrial defibrillation electrode for placement in electrical contact with the left atrium of the heart;

wherein the right atrial bipolar pacing electrode is positioned on the second lead between the right atrial pacing electrode of the first lead and the left atrial defibrillation electrode of the second lead, the right atrial bipolar pacing electrode having a first electrode and a second electrode, and the right atrial pacing electrode having a third electrode and a fourth electrode; and a cardiac stimulation device including a pulse generator that delivers defibrillation pulses between any combination of the defibrillation electrodes and pacing pulses to any one of the pacing electrodes and a sensing circuit that senses electrical activity of the heart with any one of the pacing electrodes.

2. The system of claim 1 wherein the right ventricular defibrillation electrode and the right atrial defibrillation electrode of the first lead are coil electrodes.

3. The system of claim 1 wherein the left ventricular defibrillation electrode and the left atrial defibrillation electrode of the second lead are coil electrodes.

4. The system of claim 1 wherein the defibrillation electrodes are coil electrodes.

5. The system of claim 1 wherein the cardiac stimulation device includes a conductive case and wherein the pulse generator of the cardiac stimulation device delivers defibrillation pulses between any combination of the defibrillation electrodes and the conductive case.

6. The system of claim 1 wherein the cardiac stimulation device includes a conductive case and wherein the pulse generator of the cardiac stimulation device delivers pacing pulses between any one of the pacing electrodes and the conductive case.

7. The system of claim 6 wherein the right atrial defibrillation electrode is positioned on the first lead for placement on the right atrial anterior/lateral wall.

8. The system of claim 1 wherein the second lead is implantable within the coronary sinus of the heart and wherein the left ventricular pacing electrode, the left ventricular defibrillation electrode, the left atrial pacing electrode, and the left atrial defibrillation electrode are spaced apart on the second lead so that when the left ventricular pacing electrode and the left ventricular defibrillation electrode are adjacent to the left ventricle within the coronary sinus of the heart, the left atrial pacing electrode and the left atrial defibrillation electrode are adjacent to the left atrium within the coronary sinus of the heart.

9. The system of claim 8 wherein the right ventricular defibrillation electrode and the right atrial defibrillation electrode of the first lead are coil electrodes.

10. The system of claim 8 wherein the left ventricular defibrillation electrode and the left atrial defibrillation electrode of the second lead are coil electrodes.

11. The system of claim 8 wherein the defibrillation electrodes are coil electrodes.

12. The system of claim 8 wherein the second lead includes a distal tip end and wherein the left ventricular pacing electrode is at the distal tip end of the second lead.

13. The system of claim 1 wherein the right atrial pacing electrode is proximal to the left atrial defibrillation electrode.

14. The system of claim 13 wherein the second lead further includes a left atrial bipolar pacing electrode.

15. The system of claim 14 wherein the left atrial bipolar pacing electrode is positioned on the second lead proximal to the left atrial defibrillation electrode.

16. The system of claim 1 wherein the right atrial bipolar pacing electrode is positioned on the second lead between the right atrial pacing electrode and the left atrial defibrillation electrode.

17. The system of claim 1 wherein the first lead further includes a right ventricular bipolar pacing electrode.

18. The system of claim 17 wherein the right ventricular bipolar pacing electrode is positioned on the first lead between the right ventricle pacing electrode and the right ventricular defibrillation electrode.

19. The system of claim 1 wherein the second lead further includes a left ventricular bipolar pacing electrode.

20. The system of claim 19 wherein the left ventricular bipolar pacing electrode is positioned on the second lead between the left ventricular pacing electrode and the left ventricular defibrillation electrode.

* * * * *